United States Patent
Takei et al.

(10) Patent No.: US 11,512,275 B2
(45) Date of Patent: Nov. 29, 2022

(54) SEPARATION SUBSTRATE, CELL SEPARATION FILTER, AND METHOD FOR PRODUCING PLATELET

(71) Applicant: FUJIFILM Corporation, Tokyo (JP)

(72) Inventors: Toshiki Takei, Kanagawa (JP); Tadanori Yamada, Kanagawa (JP); Ryuta Takegami, Kanagawa (JP); Kuniyuki Kaminaga, Kanagawa (JP); Akihito Fukunaga, Kanagawa (JP); Kazuhide Kanemura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 498 days.

(21) Appl. No.: 16/659,242

(22) Filed: Oct. 21, 2019

(65) Prior Publication Data
US 2020/0048597 A1 Feb. 13, 2020

Related U.S. Application Data

(63) Continuation of application No. PCT/JP2018/015924, filed on Apr. 18, 2018.

(30) Foreign Application Priority Data

May 12, 2017 (JP) .............................. JP2017-095769

(51) Int. Cl.
| | | |
|---|---|---|
| B01D 39/18 | (2006.01) | |
| C12M 1/00 | (2006.01) | |
| C12N 5/078 | (2010.01) | |
| C12N 5/00 | (2006.01) | |
| C12M 3/06 | (2006.01) | |

(52) U.S. Cl.
CPC ............. *C12M 29/04* (2013.01); *B01D 39/18* (2013.01); *C12N 5/0068* (2013.01); *C12N 5/0087* (2013.01); *C12N 5/0644* (2013.01); *B01D 2221/10* (2013.01); *B01D 2239/0618* (2013.01); *B01D 2239/0636* (2013.01); *B01D 2239/1216* (2013.01); *B01D 2239/1258* (2013.01)

(58) Field of Classification Search
CPC ........ B01D 39/18; B01D 24/00; B01D 39/00; B01D 39/04; B01D 39/14; B01D 39/16; B01D 39/1692; B01D 61/58; B01D 63/00; B01D 63/08; B01D 71/06; B01D 2257/91; C12M 3/06
See application file for complete search history.

(56) References Cited

U.S. PATENT DOCUMENTS

| | | | | |
|---|---|---|---|---|
| 5,399,268 | A | * | 3/1995 | Pall ...................... A61M 1/0209 210/806 |
| 5,601,727 | A | | 2/1997 | Bormann et al. |
| 6,177,019 | B1 | * | 1/2001 | Castino ............... A61M 1/3633 210/488 |
| 10,478,537 | B2 | | 11/2019 | Suzuki et al. |
| 2011/0065190 | A1 | | 3/2011 | Nakano et al. |
| 2013/0323712 | A1 | | 12/2013 | Sato et al. |
| 2016/0263297 | A1 | * | 9/2016 | Suzuki ................ A61M 1/3633 |

FOREIGN PATENT DOCUMENTS

| | | |
|---|---|---|
| CN | 1073614 A | 6/1993 |
| CN | 105658253 A | 6/2016 |
| JP | 2009-297023 A | 12/2009 |
| JP | 2016-192960 A | 11/2016 |
| JP | 2016-193896 A | 11/2016 |
| TW | M477285 U | 5/2014 |
| WO | WO 2015/056603 A1 | 4/2015 |
| WO | WO 2016/047444 A1 | 3/2016 |

OTHER PUBLICATIONS

International Preliminary Report on Patentability, dated Nov. 21, 2019, and Written Opinion of the International Searching Authority, dated Jul. 24, 2018, (Forms PCT/IB/326, PCT/IB/373, and PCT/ISA/237) for International Application No. PCT/JP2018/015924, with English translation.
International Search Report (Form PCT/ISA/210) for International Application No. PCT/JP2018/015924, dated Jul. 24, 2018, with English translation.
Taiwanese Office Action and Search Report for Taiwanese Application No. 107114547, dated Aug. 5, 2021, with a partial English translation.
Japanese Office Action, dated Sep. 15, 2020, for Japanese Application No. 2019-517529, with an English machine translation.
Office Action dated Jul. 4, 2022, in Chinese Patent Application No. 201880029877.X.
Taiwanese Office Action for Taiwanese Application No. 107114547, dated May 26, 2022, with a partial English translation.

* cited by examiner

*Primary Examiner* — Allison G Fitzsimmons
(74) *Attorney, Agent, or Firm* — Birch, Stewart, Kolasch & Birch, LLP

(57) ABSTRACT

An object of the present invention is to provide a separation substrate having a high megakaryocyte blocking rate and a high platelet permeation rate, and a cell separation filter and a method for producing a platelet which use the same. The separation substrate of the present invention is a separation substrate including non-woven fabric for separating a platelet from a cell suspension containing a megakaryocyte and the platelet, in which an average pore diameter of the separation substrate is 2.0 μm to 15.0 μm, and a thickness of the separation substrate is 10 μm to 500 μm.

9 Claims, No Drawings

SEPARATION SUBSTRATE, CELL SEPARATION FILTER, AND METHOD FOR PRODUCING PLATELET

CROSS-REFERENCE TO RELATED APPLICATIONS

This application is a Continuation of PCT International Application No. PCT/JP2018/015924 filed on Apr. 18, 2018, which claims priority under 35 U.S.C. § 119(a) to Japanese Patent Application No. 2017-095769 filed on May 12, 2017. The above application is hereby expressly incorporated by reference, in its entirety, into the present application.

BACKGROUND OF THE INVENTION

1. Field of the Invention

The present invention relates to a separation substrate, a cell separation filter, and a method for producing a platelet.

2. Description of the Related Art

Because platelets play a central role in the formation of blood clots and are cells having a hemostatic function in vivo, in a case where platelets decrease when bleeding occurs or when anticancer drugs are used, death may occur in severe cases.

In addition, the only established treatment for a platelet decrease is to transfuse platelet formulations. At present, platelet formulations rely on blood donation from volunteers, and it is expected that maintaining a balance between supply and demand in the medical field will be difficult because of a decrease in the population of blood-donable age groups due to a declining birthrate and an increase in the population of elderly people with high demand for blood donation, despite 4 days of a storage validity period, which is extremely short.

Accordingly, attention has been focused on the development of platelet sources that can replace blood donations.

In recent years, a technology has been reported for mass production of platelets in vitro by culturing megakaryocytes with use of pluripotent stem cells, hematopoietic precursor cells, mesenchymal lineage cells, and the like as sources.

In this technology, platelets are produced by breaking up the cytoplasm of megakaryocytes, and thereby a culture solution after platelet production contains a large number of megakaryocytes.

For this reason from the viewpoint of suppressing immunogenicity, it is necessary to develop a technology for separating megakaryocytes and platelets produced from the megakaryocytes.

As such a separation technique, for example, JP2016-192960A discloses a "separation substrate composed of a porous material for separating platelets from a cell suspension containing megakaryocytes and platelets, in which in a porous body, an average pore diameter on an inflow side is 10 μm to 20 μm, an average pore diameter decreases continuously or stepwise from the inflow side to an outflow side, and an average pore diameter on the outflow side is 3 μm to 8 μm" (claim 1).

SUMMARY OF THE INVENTION

The inventors of the present invention have examined a platelet separation substrate disclosed in JP2016-192960A, and have found that a blocking rate (a removal rate) of megakaryocytes was high, but a permeation rate (a recovery rate) of platelets was low, and there is still room for improvement in a separation performance of megakaryocytes and platelets.

An object of the present invention is to provide a separation substrate having a high megakaryocyte blocking rate and a high platelet permeation rate, and a cell separation filter and a method for producing a platelet which use the same.

As a result of intensive studies to achieve the above-mentioned object, the inventors of the present invention have found that, in a case where a separation substrate made of non-woven fabric has an average pore diameter of 2.0 μm to 15.0 μm, and a thickness of 10 μm to 500 μm, a megakaryocyte blocking rate becomes high, and a platelet permeation rate becomes high, and therefore have completed the present invention.

That is, it has been found that the above-described object can be achieved with the following configuration.

[1] A separation substrate comprising non-woven fabric for separating a platelet from a cell suspension containing a megakaryocyte and the platelet,
in which an average pore diameter of the separation substrate is 2.0 μm to 15.0 μm, and
a thickness of the separation substrate is 10 μm to 500 μm.

[2] The separation substrate according to [1], in which air permeability of the separation substrate is 2 $cm^3/cm^2/s$ to 40 $cm^3/cm^2/s$.

[3] The separation substrate according to [1] or [2], in which an average fiber diameter of a fiber forming the non-woven fabric is 800 nm to 1900 nm.

[4] The separation substrate according to any one of [1] to [3], in which a void volume of the separation substrate is 40% to 90%.

[5] The separation substrate according to any one of [1] to [4], in which the separation substrate is formed of at least one resin selected from the group consisting of a cellulose resin, a polyacrylonitrile resin, a polysulfone resin, a fluorine resin, a polyethersulfone resin, a polyamide resin, and a polyolefin resin.

[6] The separation substrate according to any one of [1] to [5], in which the separation substrate is formed of at least one resin selected from the group consisting of a cellulose resin and a polyolefin resin.

[7] The separation substrate according to [6], in which the cellulose resin is cellulose acylate or cellulose.

[8] The separation substrate according to [6], in which the polyolefin resin is polypropylene.

[9] A cell separation filter comprising: a container in which a first liquid inlet and a second liquid inlet are disposed; and a filtering medium filled between the first liquid inlet and the second liquid inlet,
in which the filtering medium is the separation substrate according to any one of [1] to [8].

[10] A method for producing a platelet, comprising:
a contact step of contacting the separation substrate according to any one of [1] to [8] with a culture solution containing at least a megakaryocyte;
a culture step of culturing a megakaryocyte to produce a platelet at least before or after the contact step; and
a recovery step of recovering a culture solution containing a produced platelet after the contact step and the culture step.

According to the present invention, it is possible to provide a separation substrate having a high megakaryocyte blocking rate and a high platelet permeation rate, and a cell separation filter and a method for producing a platelet which use the same.

DESCRIPTION OF THE PREFERRED EMBODIMENTS

Hereinafter, the present invention will be described in detail.

The explanation of the configuration requirements described below is based on representative embodiments of the present invention; however, the present invention is not intended to be limited to such embodiments.

In the present specification, a numerical value range expressed using "to" means a range including numerical values before and after "to" as a lower limit value and an upper limit value.

In general, a separation substrate is a structure having a large number of small voids therein, and examples thereof include a fiber structure, a porous membrane, a bead-filled column, and a laminate of these.

The fiber structure is a structure in which fibers are intertwined, such as woven fabric (mesh), knitted fabric, braided cord, non-woven fabric, and a fiber filled in a column. Among them, non-woven fabric is particularly preferable from the viewpoints of wide pore diameter distribution, complicated flow paths, and ease of production. Examples of methods for producing non-woven fabric include a dry method, a wet method, a spunbond method, a melt blow method, an electrospinning method, a needle punch method, and the like. Among them, from the viewpoint of productivity and versatility, the wet method, the melt blow method, and the electrospinning method are preferable.

A porous membrane has countless communication holes in the entire plastic body. Examples of manufacturing methods therefor include a phase separation method, a foaming method, an etching method of radiating radiant rays and laser light, a porogen method, a freeze-drying method, a plastic sintering method, and the like. A porous membrane obtained by using a phase separation method is particularly preferable from the viewpoint of a wide pore diameter distribution, a complicated flow path, and ease of production.

A column filled with beads is a column in which voids are formed by filling beads in the column. It is desirable that a bead particle diameter is uniform, and it is easy to control the void between the beads as the pore diameter depending on the bead particle diameter.

[Separation Substrate]

The separation substrate of the embodiment of the present invention is a separation substrate including non-woven fabric for separating a platelet from a cell suspension containing a megakaryocyte and the platelet.

In addition, an average pore diameter of the separation substrate of the embodiment of the present invention is 2.0 µm to 15.0 µm.

Furthermore, a thickness of the separation substrate of the embodiment of the present invention is 10 µm to 500 µm.

In the present specification, the "average pore diameter" is a value obtained by evaluation by increasing air pressure to 2 cc/min with respect to a sample completely wetted by GALWICK (manufactured by Porous Materials, Inc.) in a pore diameter distribution measurement test using a perm porometer (CFE-1200 AEX manufactured by Seika Corporation).

Specifically, with respect to a membrane sample completely wetted by GALWICK, a certain amount of air was fed at 2 cc/min to one side of the membrane, and while measuring a pressure thereof, a flow rate of air permeating to an opposite side of the membrane is measured.

In this method, firstly, data on pressure and permeated air flow rate (hereinafter referred to as a "wet curve") is obtained for the membrane sample wetted by GALWICK. Next, the same data (hereinafter referred to as a "dry curve") was measured for the membrane sample in a dry state, and a pressure at an intersection of a curve (half dry curve) corresponding to half of a dry curve flow rate and the wet curve is calculated. Thereafter, an average pore diameter can be calculated by introducing a surface tension ($\gamma$) of GALWICK, a contact angle ($\theta$) with the substrate, and an air pressure (P) into Formula (I).

$$\text{Average pore diameter} = 4\gamma \cos \theta / P \quad (I)$$

In addition, in the present specification, a "thickness" is a value obtained by measuring a membrane thickness of the separation substrate 10 points using a micrometer (manufactured by Mitutoyo) and averaging the respective measured values.

As described above, an average pore diameter of the separation substrate is 2.0 µm to 15.0 µm, and a thickness thereof is 10 µm to 500 µm, and thereby a megakaryocyte blocking rate becomes high and a platelet permeation rate becomes high.

The reason why such effects are exhibited is not elucidated in detail. The inventors of the present invention speculate the reason as follows.

That is, from the comparison of examples and comparative examples to be described later, it is considered that in a case where an average pore diameter of the separation substrate is 15.0 µm or less, permeation of megakaryocytes can be prevented, and in a case where an average pore diameter of the separation substrate is 2.0 µm or more and a thickness of the separation substrate is 10 µm to 500 µm, platelets can be permeated.

An average pore diameter of the separation substrate of the embodiment of the present invention is preferably 3.0 to 11.0 µm, and is more preferably 4.0 to 9.0 µm.

In addition, a thickness of the separation substrate of the embodiment of the present invention is preferably 20 to 300 µm, and is more preferably 20 to 190 µm.

In the present invention, air permeability of the separation substrate is preferably 2 $cm^3/cm^2/s$ to 40 $cm^3/cm^2/s$, and is more preferably 5 $cm^3/cm^2/s$ to 30 $cm^3/cm^2/s$, because a separation performance of megakaryocytes and platelets is further improved.

In the present specification, the term "air permeability" refers to a value measured by the fragile method described in "General Non-Woven Fabric Testing Method" of JIS L 1913.

In addition, in the present invention, a void volume of the separation substrate is preferably 40% to 90%, and is more preferably more than 50% and less than 85%, because a separation performance of megakaryocytes and platelets is further improved.

In the present specification, a "void volume" means a value calculated by the following equation.

$$\text{Void volume (\%)} = [1 - \{m/\rho/(S \times d)\}] \times 100$$

m: Sheet weight (g)
$\rho$: Resin density (g/$cm^3$)
S: Sheet area ($cm^2$)
d: Sheet thickness (cm)

As described above, the structure of the separation substrate of the embodiment of the present invention is a non-woven fabric.

Examples of methods for producing non-woven fabric include an electrospinning method, a composite melt spinning method, a melt blow method, and a chemical vapor deposition (CVD) method. Among them, the electrospinning method is preferable.

Specifically, for example, a non-woven fabric 120 can be manufactured by a nanofiber manufacturing apparatus 110 shown in FIG. 1 of JP2016-053232A.

In the present invention, an average fiber diameter of the fibers constituting the non-woven fabric is preferably 800 nm to 1,900 nm, because sufficient fiber strength and favorable separation performance can be achieved at the same time.

In addition, it is preferable that an average fiber length of the fibers constituting the non-woven fabric is 1 mm to 1 m, because the separation of the fibers can be prevented in a case where the separation substrate is used (for example, during filtration).

The average fiber diameter and the average fiber length can be adjusted by adjusting a concentration of a raw material (for example, cellulose acetate) solution for producing the non-woven fabric.

The average fiber diameter means a value measured as follows.

The surface of non-woven fabric formed from fibers is observed by taking a Transmission Electron Microscope (TEM) image or a Scanning Electron Microscope (SEM) image.

An observation based on an electron microscopic image is performed at a magnification ratio selected from 1,000 times to 5,000 times depending on the size of the constituent fiber. However, the sample, the observation conditions, and the magnification ratio are adjusted so as to satisfy the following conditions.

(1) One straight line X is drawn at an arbitrary site within an image to be observed, and 20 or more fibers intersect this straight line X.

(2) A straight line Y perpendicularly intersecting the straight line X is drawn in the same image, and 20 or more fibers intersect the straight line Y.

In regard to the electron microscopic observation images such as described above, for each of the fibers intersecting the straight line X and the fibers intersecting the straight line Y, widths (minor axis of the fiber) of at least 20 fibers (that is, at least 40 fibers in total) are read out. In this manner, an observation of at least 3 sets or more of the electron microscopic images such as described above is made, and fiber diameters of at least 40 fibers×3 sets (that is, at least 120 fibers) are read out.

The average fiber diameter is determined by averaging the fiber diameters read out as such.

The average fiber length means a value measured as follows.

That is, the fiber length of the fiber can be determined by analyzing the electron microscopic observation image used on the occasion of measuring the average fiber diameter described above.

Specifically, in the electron microscopic observation image such as described above, for each of the fibers intersecting the straight line X and the fibers intersecting the straight line Y, fiber lengths of at least 20 fibers (that is, at least 40 fibers in total) are read out.

In this manner, an observation of at least 3 sets or more of the electron microscopic images such as described above is made, and the fiber lengths of at least 40 fibers×3 sets (that is, at least 120 fibers) are read out.

The average fiber length is determined by averaging the fiber lengths read out as such.

The separation substrate of the embodiment of the present invention is preferably composed of a resin material. Specific examples of resin materials include cellulose resins such as cellulose acylate and cellulose; polyacrylonitrile resins; polysulfone resins; fluorine resins; polyethersulfone resins; polyamide resins; polyolefin resins such as polypropylene; and the like. These may be used alone or in combination of two or more kinds thereof.

Among them, the separation substrate is preferably composed of at least one of a cellulose resin and a polyolefin resin, is more preferably composed of a cellulose resin, and is even more preferably composed of cellulose acylate or cellulose. In addition, a polyolefin resin is preferably polypropylene.

In the present invention, the separation substrate composed of cellulose can also be obtained by saponifying the separation substrate composed of cellulose acylate.

Specific examples of acyl groups included in cellulose acylate include an acetyl group, a propionyl group, a butyryl group, and the like. The acyl groups to be substituted may be composed only of a single kind (for example, only an acetyl group) or may be of two or more kinds.

In the present invention, from the viewpoint of suppressing the adsorption of platelets to the separation substrate and further improving the permeation rate of platelets, the surface of the separation substrate is subjected to hydrophilic treatment, and a low-platelet-adsorption material may be chemically or physically modified.

The low-platelet-adsorption material is preferably a polymer having a hydrophilic group in the side chain. Examples thereof include 2-methacryloyloxyethyl phosphorylcholine, ethylene glycol, methyl methacrylate, hydroxyethyl methacrylate, vinyl alcohol, N-vinyl-2-pyrrolidone, a polymer of a sulfobetaine monomer, and the like.

Specific examples of hydrophilic groups include a hydroxyl group, an ether group, a nitro group, an imino group, a carbonyl group, a phosphoric acid group, a methoxydiethylene glycol group, a methoxytriethylene glycol group, an ethoxydiethylene glycol group, an ethoxytriethylene glycol group, an amino group, a dimethylamino group, a diethylamino group, a carboxyl group, a phosphoryl group, a phosphorylcholine group, a sulfone group, and salts thereof.

Furthermore, as a low-platelet-adsorption material and a modification method thereof, materials and methods disclosed in WO87/005812A, JP1992-152952A (JP-H04-152952A), JP1993-194243A (JP-H05-194243A), WO2010/113632A, and the like can be used.

[Cell Suspension]

The cell suspension used for the separation of platelets using the separation substrate of the embodiment of the present invention is a cell suspension containing megakaryocytes and platelets.

Megakaryocytes and platelets are not particularly limited, and examples thereof include megakaryocytes and platelets collected from adult tissue; megakaryocytes and platelets differentiated from cells having differentiation ability such as pluripotent stem cells, hematopoietic precursor cells, and mesenchymal cells; megakaryocytes and platelets produced by using direct reprogramming techniques on cells that do not have the ability to differentiate into megakaryocytes by methods of the related art; megakaryocytes and platelets combining these; and the like.

Examples of pluripotent stem cells include embryonic stem cells ((ES) cells), nuclear transfer embryonic stem cells ((nt) ES cells), and induced pluripotent stem cells ((iPS)

cells), and the like. Among them, induced pluripotent stem cells (iPS cells) are preferable.

Examples of hematopoietic precursor cells include cells derived from bone marrow, cells derived from umbilical cord blood, cells derived from (granulocyte-colony stimulating factor: G-CSF)-mobilized peripheral blood, middle lobe lung cells derived from ES cells, cells derived from peripheral blood, and the like, but are not limited thereto. Examples of these hematopoietic precursor cells include cells positive to cluster of differentiation (CD) 34 (for example, CD34+ cells, CD133+ cells, SP cells, CD34+ CD38− cells, c-kit+ cells, or CD3−, CD4−, CD8−, and CD34+ cells) (WO2004/110139A).

Examples of mesenchymal cells include mesenchymal stem cells, adipose precursor cells, bone marrow cells, adipocytes and synovial cells, among which adipose precursor cells are preferable.

Examples of cells that do not have an ability to be differentiated into megakaryocytes by general methods include fibroblasts and the like, but are not limited thereto.

[Cell Separation Filter]

The cell separation filter of the embodiment of the present invention is a cell separation filter including a container in which a first liquid inlet and a second liquid inlet are disposed; and a filtering medium filled between the first liquid inlet and the second liquid inlet, in which the separation substrate of the embodiment of the present invention described above is used for the filtering medium.

A form, size, and material of the container used for the cell separation filter are not particularly limited.

A form of the container may be any form such as, for example, a sphere, a container, a cassette, a bag, a tube, or a column.

As the container type, any of a cross flow type and a column type can be used.

[Method for Producing Platelet]

The method for producing a platelet of the embodiment of the present invention includes a contact step of contacting the separation substrate of the embodiment of the present invention described above with a culture solution containing at least a megakaryocyte;

a culture step of culturing a megakaryocyte to produce a platelet before and/or after the contact step; and a recovery step of recovering a culture solution containing a produced platelet after the contact step and the culture step.

A contact means in the contact step can be appropriately selected according to the amount of the culture solution and the concentration of megakaryocytes. Examples thereof include a method of supplying a cell suspension to a tower or column filled with the separation substrate of the embodiment of the present invention.

In addition, examples of means for producing platelets in the culture step include a method of applying a shear stress by a fluid, and specifically, a method of stirring a culture solution containing megakaryocytes. Furthermore, the megakaryocyte cultured in the culture step may be a megakaryocyte supplemented with the separation substrate of the embodiment of the present invention, in a case where the culture step is performed after the contact step. Furthermore, in a case where the culture step is performed after the contact step, as will be described later in examples, it is considered that in a case where the cell suspension containing megakaryocytes and platelets is brought into contact with the separation substrate, platelets are produced in megakaryocytes captured in the initial stage even by loading due to the cell suspension (for example, a fluid) that comes into contact therewith.

Furthermore, examples of recovery means in the recovery step include a method of passing a culture solution containing the produced platelets through a column or column filled with the separation substrate of the embodiment of the present invention.

EXAMPLES

Hereinafter, the present invention will be described in more detail based on Examples. The materials, amounts used, proportions, treatments, treatment procedures, and the like disclosed in the following Examples can be modified as appropriate as long as the gist of the present invention is maintained. Therefore, the scope of the present invention should not be limitedly interpreted by the Examples described below.

Example 1

<Synthesis of Cellulose Acetate>

Cellulose (raw material: cotton linter) was mixed with acetate, acetic anhydride, and sulfuric acid, and the mixture was acetylated while a reaction temperature was maintained at 40° C. or lower. After the raw material cellulose disappeared and acetylation was completed, the system was further heated continuously at a temperature of 40° C. or lower, and the degree of polymerization was adjusted to a desired value.

Next, residual acid anhydride was hydrolyzed by adding an aqueous solution of acetate, and then partial hydrolysis was performed by heating at a temperature of 60° C. or lower. Thus, a degree of substitution was adjusted to a desired degree.

Residual sulfuric acid was neutralized with an excess amount of magnesium acetate. Reprecipitation from the aqueous solution of acetate was performed, and washing with water was repeated. Thus, a cellulose acetate having a substitution degree of 2.91 was synthesized.

<Synthesis of Cellulose Acetate Propionate>

A cellulose acetate propionate having an acetyl substitution degree of 1.3% and a propionyl substitution degree of 48% was synthesized in the same manner as the synthesis of cellulose acetate, except that an acetate was changed to a mixed solvent of acetate and propionate, and acetic anhydride was changed to a mixture of acetic anhydride and propionic anhydride.

<Production of Non-Woven Fabric>

The cellulose acetate thus synthesized was dissolved in a mixed solvent of 87% of dichloromethane and 13% of methanol to prepare a cellulose acetate solution having a concentration of 3.5 g/100 cm$^3$, and it was set in a part of a plurality of nozzles of a nanofiber manufacturing apparatus.

The cellulose acetate propionate solution prepared in the same manner was set in the remaining nozzles, and a non-woven fabric composed of cellulose acetate fibers and cellulose acetate propionate having a basis weight of 10 g/m$^2$ and 20×30 cm was produced.

Next, the produced non-woven fabric was subjected to heat treatment at 200° C. for 5 minutes to produce a separation substrate.

<Megakaryocytes and Platelets>

Medium: A medium in which 50 ml of bovine serum (Life Technologies) was added to 450 ml of RPMI1640 (Life Technologies) was used.

Megakaryocyte: MEG-01 (ATCC) was used as the megakaryocyte. A megakaryocyte liquid (6×10$^5$ cells/ml) was prepared by mixing this with a medium.

Platelet suspension: A platelet suspension isolated from rat peripheral blood was used as platelets. Specifically, 10 ml of whole blood collected from a rat was recovered in a 15 ml conical tube for centrifugation (manufactured by Falcon) which contains a citrate-dextrose solution (ACD) (manufactured by Sigma-Aldrich). Centrifugation was performed at 300×g and room temperature for 7 minutes, and the plasma layer and the Buffy coat layer after centrifugation were recovered. The recovered solution was centrifuged in the same manner, and only the Plasma layer was recovered, and then centrifuged at 1800×g at room temperature for 5 minutes, and the supernatant was recovered to obtain platelets. This was mixed with a medium to prepare a platelet suspension ($6 \times 10^7$ cells/ml).

A cell suspension was prepared by mixing equal volumes of megakaryocyte fluid and platelet suspension.

<Cell Separation Test>

Membrane separation treatment was performed using a filtration module in which one flow port on the supply side of a filtration module (ADVANTEC, KS-47) was connected to a 50 ml syringe (Terumo) containing a cell suspension. The syringe was placed in a syringe pump (HARVARD APPARATUS, PHD ULTRA 4400), and the syringe pump was operated so that 30 ml of the cell suspension was supplied at a flow rate of 3 ml/min in a dead-end manner that goes straight to the separation substrate installed in the filtration module. The filtrate discharged from the permeate side outlet of the filtration module was recovered.

<Count of the Number of Recovered Cells>

100 µl of filtrate collected from the permeate side of the filtration module was added to 10 µl of Dulbecco's Phosphate-Buffered Saline (DPBS) (manufactured by Thermo Fisher Scientific) in which Hoechst 33342 (manufactured by Dojindo Laboratories), which is a nuclear stain, was added, and the mixture was reacted for 15 minutes in a light-shielded environment. 300 µl of DPBS was added thereto, and measurement was performed by flow cytometry (FACS Aria) by using BD Trucount tubes (manufactured by Nippon Becton, Dickinson and Company).

Megakaryocyte fraction and platelet fraction were determined from forward scatter (FSC) and side scatter (SSC) gates. Nuclear stain negative cells in the platelet fractions are perceived as platelets, and nuclear stain positive cells in the megakaryocyte fractions are perceived as megakaryocytes. Therefore, the number of platelets and the number of megakaryocytes in the recovered solution was calculated.

A platelet permeation rate and a megakaryocyte blocking rate obtained from the following equation are shown in Table 1.

Platelet permeation rate (%)=(the number of platelets in filtrate/the number of platelets in original solution)×100

Megakaryocyte blocking rate (%)=100−(number of megakaryocytes in filtrate/number of megakaryocytes in original solution)×100

<Evaluation (Separation Judgment)>

As a general judgment of separation, the following criteria were evaluated. The results are shown in Table 1.

A: A platelet permeation rate is 80% or more, and a megakaryocyte blocking rate is 95% or more.

B: A platelet permeation rate is 80% or more, and a megakaryocyte blocking rate is 90% or more.

Alternatively, a platelet permeation rate is 70% or more, and a megakaryocyte blocking rate is 95% or more.

C: A platelet permeation rate is less than 70%, or a megakaryocyte blocking rate is less than 90%.

Examples 2 to 5 and Comparative Example 1

A separation substrate was produced and evaluated in the same manner as in Example 1 except that the non-woven fabric was produced by adjusting the concentrations of the cellulose acetate and the cellulose acetate propionate solution introduced into the nanofiber manufacturing apparatus. The results are shown in Table 1.

Examples 6 and 7 and Comparative Examples 2 and 3

A separation substrate was produced and evaluated in the same manner as in Example 1 except that a basis weight for producing the non-woven fabric was changed using the nanofiber manufacturing apparatus. The results are shown in Table 1.

Examples 8 and 9 and Comparative Example 4

Evaluation was performed in the same manner as in Example 1 using polypropylene non-woven fabric (manufactured by 3M) in Examples 8 to 9 and using polypropylene non-woven fabric (manufactured by Merck Millipore) in Comparative Example 4. The results are shown in Table 1.

Example 10

A separation substrate was produced and evaluated in the same manner as in Example 1 except that non-woven fabric was produced using a cellulose solution dissolved in a mixed solvent of 87% dichloromethane and 13% methanol. The results are shown in Table 1.

Example 11 and Comparative Example 5

A separation substrate was produced and evaluated in the same manner as in Example 1 except that non-woven fabric was produced using a polyacrylonitrile solution dissolved in N,N-dimethylformamide (DMF). The results are shown in Table 1.

Comparative Examples 6 to 8

Evaluation was performed in the same manner as in Example 1 except that a polyethylene terephthalate non-woven fabric (manufactured by Teijin) was used in Comparative Example 6, a twill woven mesh made of SUS316 was used in Comparative Example 7, and a porous membrane made of cellulose acetate (ADVANTEC) was used in Comparative Example 8. The results are shown in Table 1.

Comparative Example 9

Comparative Example 9 used data obtained by quoting the data of Example 3 of JP2016-192960A as a prior example, partially modified data was used.

In each example, the filtration membrane was made different as shown in Table 1.

Specifically, in Examples 1 to 5 and Comparative Example 1, non-woven fabrics made of cellulose acylate having different pore diameters and air permeability were used.

In Examples 6 and 7 and Comparative Examples 2 and 3, non-woven fabrics made of cellulose acylate having different thicknesses were used.

In Examples 8 and 9 and Comparative Example 4, non-woven fabrics made of polypropylene having different average pore diameters were used.

In Examples 10 and 11 and Comparative Examples 5 and 6, non-woven fabrics of different materials were used.

In Comparative Example 7, a separation substrate having a mesh structure was used, and in Comparative Example 8, a separation substrate having a porous structure was used.

Furthermore, it was found that, even in a case where the average pore diameter is 2.0 μm to 15.0 μm and the thickness is 10 μm to 500 μm, in a case of using a separation substrate that is not in the form of a non-woven fabric, any one of a platelet permeation rate or the megakaryocyte blocking rate becomes low (Comparative Examples 7 and 8).

On the other hand, it was found that, in a case of using a separation substrate made of a non-woven fabric having an

TABLE 1

| | Material | Structure | Average pore diameter (μm) | Average fiber diameter (nm) | Thickness (μm) |
|---|---|---|---|---|---|
| Example 1 | Cellulose acetate/cellulose acetate propionate | Non-woven fabric | 4.2 | 902 | 40 |
| Example 2 | Cellulose acetate/cellulose acetate propionate | Non-woven fabric | 8.0 | 1260 | 25 |
| Example 3 | Cellulose acetate/cellulose acetate propionate | Non-woven fabric | 8.7 | 1058 | 48 |
| Example 4 | Cellulose acetate/cellulose acetate propionate | Non-woven fabric | 9.0 | 1786 | 23 |
| Example 5 | Cellulose acetate/cellulose acetate propionate | Non-woven fabric | 12.0 | 1337 | 53 |
| Example 6 | Cellulose acetate/cellulose acetate propionate | Non-woven fabric | 8.5 | 1041 | 192 |
| Example 7 | Cellulose acetate/cellulose acetate propionate | Non-woven fabric | 8.6 | 1082 | 461 |
| Example 8 | Polypropylene | Non-woven fabric | 7.8 | 1810 | 135 |
| Example 9 | Polypropylene | Non-woven fabric | 14.3 | 1727 | 51 |
| Example 10 | Cellulose | Non-woven fabric | 8.7 | 1058 | 32 |
| Example 11 | Polyacrylonitrile | Non-woven fabric | 2.8 | 1041 | 16 |
| Comparative Example 1 | Cellulose acetate/cellulose acetate propionate | Non-woven fabric | 17.4 | 1904 | 10 |
| Comparative Example 2 | Cellulose acetate/cellulose acetate propionate | Non-woven fabric | 8.6 | 1074 | 528 |
| Comparative Example 3 | Cellulose acetate/cellulose acetate propionate | Non-woven fabric | 8.4 | 1109 | 830 |
| Comparative Example 4 | Polypropylene | Non-woven fabric | 1.2 | 2201 | 113 |
| Comparative Example 5 | Polyacrylonitrile | Non-woven fabric | 1.2 | 298 | 14 |
| Comparative Example 6 | Polyethylene terephthalate | Non-woven fabric | 1.1 | 700 | 25 |
| Comparative Example 7 | SUS316 | Mesh | 8.4 | | 60 |
| Comparative Example 8 | Cellulose acetate | Porous membrane | 3.0 | | 40 |
| Comparative Example 9 | Polypropylene | Non-woven fabric | 10.4 | 2200 | 630 |

| | Void volume (%) | Air permeability (cm³/cm²/sec) | Platelet permeation rate | Megakaryocyte blocking rate | Evaluation |
|---|---|---|---|---|---|
| Example 1 | 80 | 6.5 | 81.1% | 99.9% | A |
| Example 2 | 64 | 21.7 | 94.6% | 99.1% | A |
| Example 3 | 83 | 21.8 | 94.6% | 99.4% | A |
| Example 4 | 66 | — | 98.4% | 98.5% | A |
| Example 5 | 85 | 31.7 | 99.0% | 91.9% | B |
| Example 6 | 83 | — | 91.1% | 99.6% | A |
| Example 7 | 84 | — | 87.9% | 99.8% | A |
| Example 8 | 61 | — | 91.8% | 99.7% | A |
| Example 9 | 56 | — | 94.0% | 91.0% | B |
| Example 10 | 86 | — | 95.4% | 99.7% | A |
| Example 11 | 47 | 2.5 | 74.6% | 99.8% | B |
| Comparative Example 1 | 60 | 48.1 | 98.0% | 68.9% | C |
| Comparative Example 2 | 83 | — | 66.5% | 99.8% | C |
| Comparative Example 3 | 82 | — | 50.3% | 99.8% | C |
| Comparative Example 4 | 24 | — | 62.2% | 99.9% | C |
| Comparative Example 5 | 81 | — | 3.6% | 100.0% | C |
| Comparative Example 6 | 42 | 0.4 | 4.4% | 99.9% | C |
| Comparative Example 7 | 40 | — | 95.7% | 87.9% | C |
| Comparative Example 8 | 65 | — | 37.2% | 99.9% | C |
| Comparative Example 9 | 88 | — | 65.9% | 99.9% | C |

Based on the results shown in Table 1, it was found that, in a case where a separation substrate made of a non-woven fabric having an average pore diameter larger than 15 μm was used, a blocking rate of megakaryocytes becomes low (Comparative Example 1).

In addition, it was found that, in a case where a separation substrate made of a non-woven fabric having an average pore diameter of less than 2.0 μm was used, the platelet permeation rate becomes low (Comparative Examples 4 to 6).

Furthermore, it was found that, in a case where a separation substrate made of a non-woven fabric having a thickness of more than 500 μm was used, the platelet permeation rate becomes low (Comparative Examples 2, 3, and 9).

average pore diameter of 2.0 μm to 15.0 μm and a thickness of 10 μm to 500 μm, the megakaryocyte blocking rate becomes high, and the platelet permeation rate becomes high (Examples 1 to 11).

What is claimed is:

1. A method for producing a platelet, comprising:
    a production step of producing a platelet from a megakaryocyte;
    a contact step of contacting a separation substrate with a culture solution containing at least the megakaryocyte and the platelet;
    and
    a recovery step of recovering, as a filtrate, a culture solution containing a produced platelet separated by the separation substrate after the contact step;

wherein the separation substrate comprises non-woven fabric including cellulose acylate containing two or more acyl groups for separating a megakaryocyte and a platelet from a cell suspension containing the megakaryocyte and the platelet, blocking the megakaryocyte at a rate of 90% or more, and recovering the platelets, an average pore diameter of the separation substrate is 2.0 μm to 15.0 μm, and a thickness of the separation substrate is 10 μm to 500 μm.

2. The method for producing a platelet according to claim 1, wherein air permeability of the separation substrate is 2 cm$^3$/cm$^2$/s to 40 cm$^3$/cm$^2$/s.

3. The method for producing a platelet according to claim 1, wherein air permeability of the separation substrate is 5 cm$^3$/cm$^2$/s to 30 cm$^3$/cm$^2$/s.

4. The method for producing a platelet according to claim 1, wherein an average fiber diameter of a fiber forming the non-woven fabric is 800 nm to 1900 nm.

5. The method for producing a platelet according to claim 1, wherein a void volume of the separation substrate is 40% to 90%.

6. The method for producing a platelet according to claim 1, wherein a void volume of the separation substrate is more than 50% and less than 85%.

7. The method for producing a platelet according to claim 1, wherein the platelet permeation rate of the separation substrate is 80% or more.

8. The method for producing a platelet according to claim 1, wherein the non-woven fabric is a non-woven fabric produced by an electrospinning method.

9. The method for producing a platelet according to claim 1, wherein the non-woven fabric is a single-layer non-woven fabric.

* * * * *